United States Patent [19]

Lee, Jr.

[11] Patent Number: 5,077,780

[45] Date of Patent: Dec. 31, 1991

[54] FLAT TOP RADIOGRAPHIC TABLE

[76] Inventor: James G. Lee, Jr., 7815 Baltusrol La., Charlotte, N.C. 28210

[21] Appl. No.: 617,503

[22] Filed: Nov. 23, 1990

[51] Int. Cl.$^5$ .......................... H05G 1/02; A61G 7/08
[52] U.S. Cl. ...................................... 378/196; 378/20; 378/177; 378/208; 378/178; 5/81 R; 5/81 B; 5/89; 108/65
[58] Field of Search ................... 378/20, 68, 195, 196, 378/198, 177, 180, 208, 209, 17 B; 5/81 K, 81 B, 89; 108/65

[56] References Cited

U.S. PATENT DOCUMENTS

| | | | |
|---|---|---|---|
| 3,967,126 | 6/1976 | Otto, Jr. .............................. | 378/177 |
| 4,208,586 | 6/1980 | Craig et al. .......................... | 378/189 |
| 4,365,345 | 12/1982 | Craig et al. .......................... | 378/190 |
| 4,392,096 | 7/1983 | Grajewski et al. ................. | 378/179 |
| 4,475,072 | 10/1984 | Schwehr et al. ...................... | 378/17 |
| 4,602,378 | 6/1986 | Kelman et al. ....................... | 378/26 |
| 4,700,938 | 10/1987 | Chambron .......................... | 378/209 |
| 4,773,637 | 9/1988 | Jarin .................................... | 269/322 |
| 4,893,323 | 1/1990 | Cook, III ............................ | 378/208 |

OTHER PUBLICATIONS

Flat-top Tables, TransWorld Radiographic X-Ray Systems, TransWorld X-Ray Corporation, Charlotte, NC.

Primary Examiner—Edward P. Westin
Assistant Examiner—Don Wong
Attorney, Agent, or Firm—Bell, Seltzer, Park & Gibson

[57] ABSTRACT

A flat top radiographic table includes a pair of longitudinal frame members which grip a thin panel at opposite ends thereof. The longitudinal frame members grip the thin panel at its bottom and side edges only, with the panel being free of support of the frame members at the panel top. The table top is thereby made coplanar to simplify transfer of a patient to and from the table. The frame members preferably grip the panel via a pair of projections which mate with a pair of recesses on the side edges and bottom of the thin panel.

23 Claims, 3 Drawing Sheets

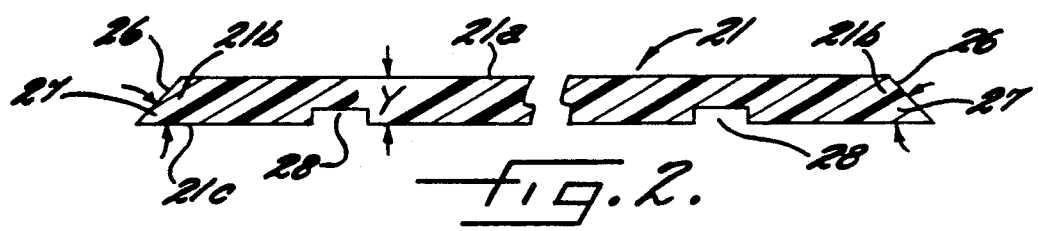
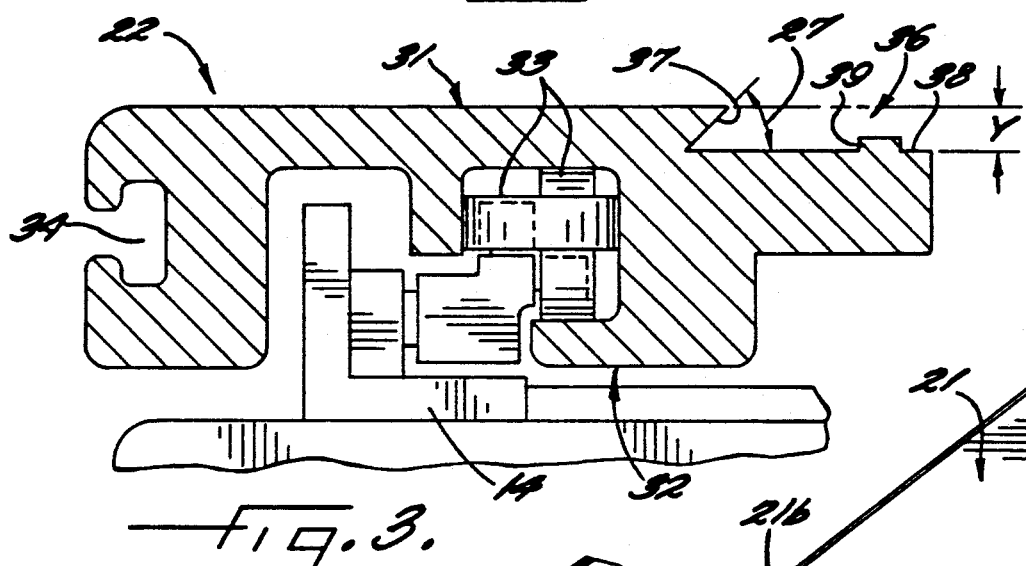
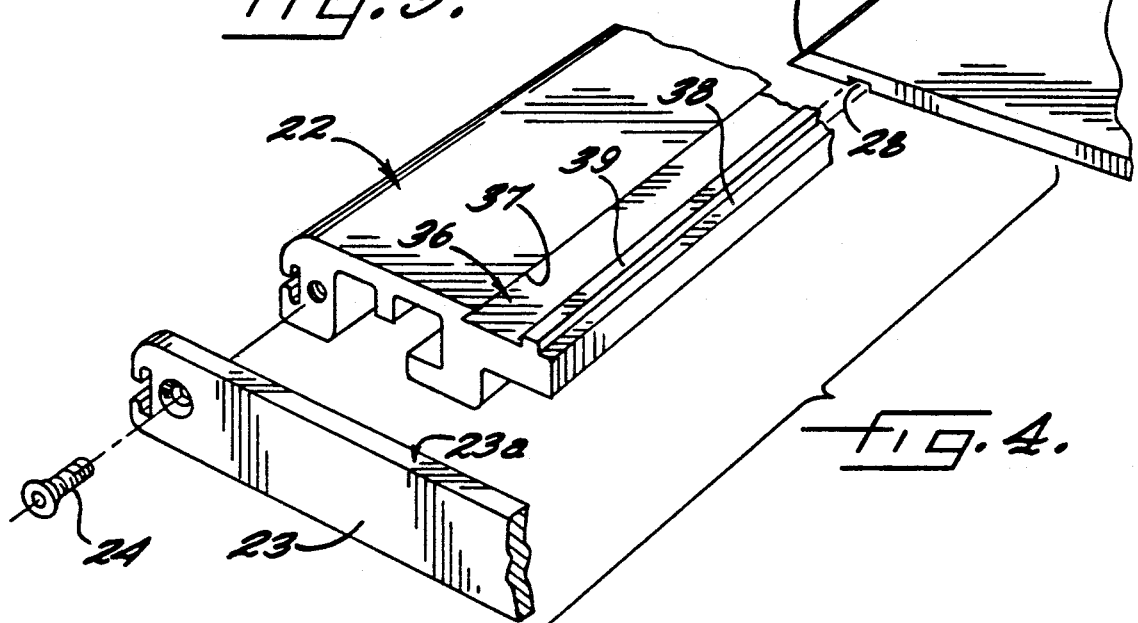
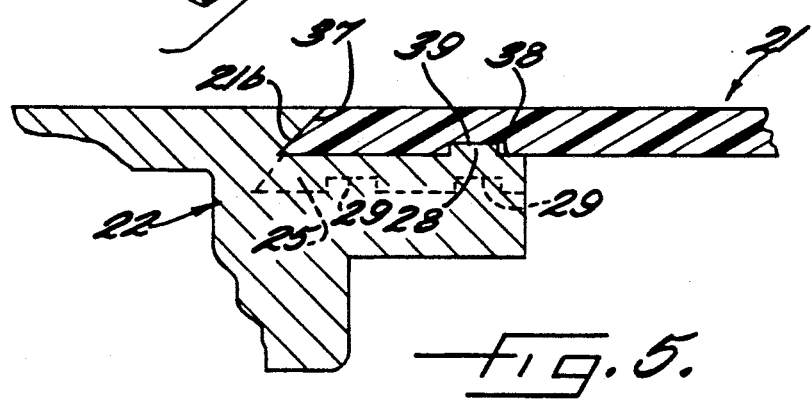

FLAT TOP RADIOGRAPHIC TABLE

FIELD OF THE INVENTION

This invention relates to radiographic systems such as x-ray systems, and more particularly to patient supporting tables for radiographic systems.

BACKGROUND OF THE INVENTION

Patient supporting tables are used extensively in many medical related applications such as surgery, examination and therapy. They are also used for patient support in radiographic systems, such as x-ray systems. More particularly, a typical x-ray system includes an x-ray table having a top upon which a patient is positioned. The table top is typically moveable laterally and longitudinally for ease of patient positioning. An x-ray source is generally positioned above the table top and an x-ray film cassette or other image recorder is positioned below the table top.

The x-ray table must fulfil a number of often conflicting design requirements. For example, the underside surface of the table top must be free of obstructions so that the table top can be moveable relative to the x-ray apparatus to allow for patient positioning. The table top also must be thin so that the x-ray film may be placed as close to the patient as possible The table top must also be constructed of a material which is relatively transparent to x-rays so that a high quality image may be obtained. Also, the table must be able to support a person weighing up to 400 pounds.

In order to accommodate these conflicting design requirements, known x-ray table tops have been constructed of a thin panel of a paper base resinous material. The resinous panel is sufficiently thin ($\frac{3}{8}$" or less in thickness) to provide minimal attenuation of x-rays and to allow the x-ray film to be positioned close to the patient. The panel is suspended only at its ends by a pair of longitudinally extending frame members so that unobstructed movement of the top may be obtained. The longitudinally extending frame members grip the panel so that the thin panel can support a human being without collapsing. X-ray tables as described above are illustrated in U.S. Pat. Nos. 3,967,126 to Otto, Jr., 4,208,586 to Craig et al., and 4,365,345 to Craig et al.

In order to adequately support the thin panel, the frame members of the above described tables have gripped the panel on the top surface and on the bottom surface thereof. Accordingly, the longitudinal frame members included panel gripping surfaces above and below the panel. The gripping surface above the panel produced a lip in the frame members, rising above the top surface of the panel and extending longitudinally along the entire length of the panel. As a result of this longitudinal lip it has been difficult to transfer a patient directly from a stretcher or other table onto the x-ray table. This lip also made it difficult to transfer a patient from the x-ray table back to a stretcher.

The lip also presents problems for positioning the x-ray source and the x-ray film during various radiological procedures. For example when obtaining a lateral spine x-ray of a patient lying on his back on the table top, the x-ray source must be positioned to emit x-rays parallel to the table top and centered about $\frac{1}{2}$" above the table top in order to center the x-rays on the spine. In this procedure, the lip interferes with passage of the x-rays. Also, when obtaining an x-ray of an extremity such as a lower leg, the x-ray film is typically positioned on the table top, with the extremity lying on the film. In this procedure, the lip interferes with the positioning of the x-ray film. Unfortunately, to the best of Applicant's knowledge, the lip on the table top has heretofore been essential because the longitudinal frame members had to grip the top and bottom surfaces of the thin panel.

SUMMARY OF THE INVENTION

It is therefore an object of the present invention to provide an improved table top for a radiographic system.

It is yet another object of the present invention to provide a radiographic table having a thin table top panel which is supported at the periphery thereof to reduce radiographic attenuation and allow unrestricted patient positioning on the table top.

It is still another object of the present invention to provide a thin panel radiographic table which eliminates the need for a lip on the top surface of the longitudinal frame members.

These and other objects are provided according to the present invention by a radiographic table top in which the longitudinal frame members are able to grip the thin panel extending therebetween at the bottom and side edges of the panel only, with the panel being free of support of the frame members at the panel top. Accordingly, the top of the frame members and the panel top are coplanar, to thereby provide a flat top radiographic table. The flat top radiographic table simplifies transfer of a patient to and from the radiographic table, and allows an x-ray source and film to be positioned without interference from a lip on the table top.

According to the invention, each of the longitudinal frame members and the panel include mating surfaces thereon, with the mating surfaces being configured to mechanically lock the frame members to the panel such that the frame member top surfaces and the panel top surface lie in a single plane to provide a flat top radiographic table. The frame member mating surfaces may comprise a pair of projections, and the panel mating surfaces may comprise a pair of recesses at each longitudinal end thereof, with the pair of projections on a respective frame member mating with the pair of recesses on the respective ends of the panel. Each pair of recesses may comprise a first recess on the side edge of the panel and a second recess on the panel bottom surface near the side edge, and in particular may comprise an elongated bevel in the panel side edge and an elongated groove in the panel bottom near the side edge. Elongated projections on the frame members may be positioned to mate with the bevel and groove to support the panel without gripping the top surface of the panel.

In particular, each of the longitudinal frame members includes a ledge in the top surface thereof with the ledge including a side ledge surface and a top ledge surface. The side ledge surface is oriented at an acute angle relative to the top ledge surface, and the top ledge surface includes a projection such as a longitudinal tongue thereon. The longitudinal side edges of the panel are bevelled so that the side edges are oriented at the acute angle relative to the panel bottom surface, and the panel bottom surface also includes a longitudinal groove therein which is oriented relative to the panel side edges to accept the longitudinal tongue therein. The thickness of the recessed ledge is equal to the thickness of the panel so that a flat top radiographic table is provided.

In one embodiment the longitudinal tongue in the frame member is mechanically fixed relative to the frame member and the thin table top panel is mated to the frame member by sliding the beveled side edge and groove longitudinally along the ledge side and tongue. In another embodiment, the longitudinal frame member includes a moveable tongue so that the beveled side edge of the panel may be placed against the ledge side without sliding. Double sided tape or other adhesive may be used to hold the panel to the frame and the moveable tongue may be adjusted to grip the panel in the recess and hold it in place. A flat, thin, unobstructed table top is thereby provided for radiographic applications.

BRIEF DESCRIPTION OF THE DRAWINGS

FIG. 2 is a cross-sectional view of the thin table top panel of FIG. 1 taken along line AA'.

FIG. 3 is a cross-sectional view of a first embodiment of the table top longitudinal frame member of FIG. 1, taken along line AA'.

FIG. 4 is an exploded perspective view illustrating assembly of the panel of FIG. 2 and the frame member of FIG. 3.

FIG. 5 is a cross sectional view, taken along line AA', of the table top of FIG. 2 and the frame member of FIG. 3, assembled together.

DESCRIPTION OF A PREFERRED EMBODIMENT

The present invention now will be described more fully hereinafter with reference to the accompanying drawings, in which a preferred embodiment of the invention is shown. This invention may, however, be embodied in many different forms and should not be construed as limited to the embodiment set forth herein; rather, this embodiment is provided so that this disclosure will be thorough and complete, and will fully convey the scope of the invention to those skilled in the art. Like numbers refer to like elements throughout.

Figure 1:
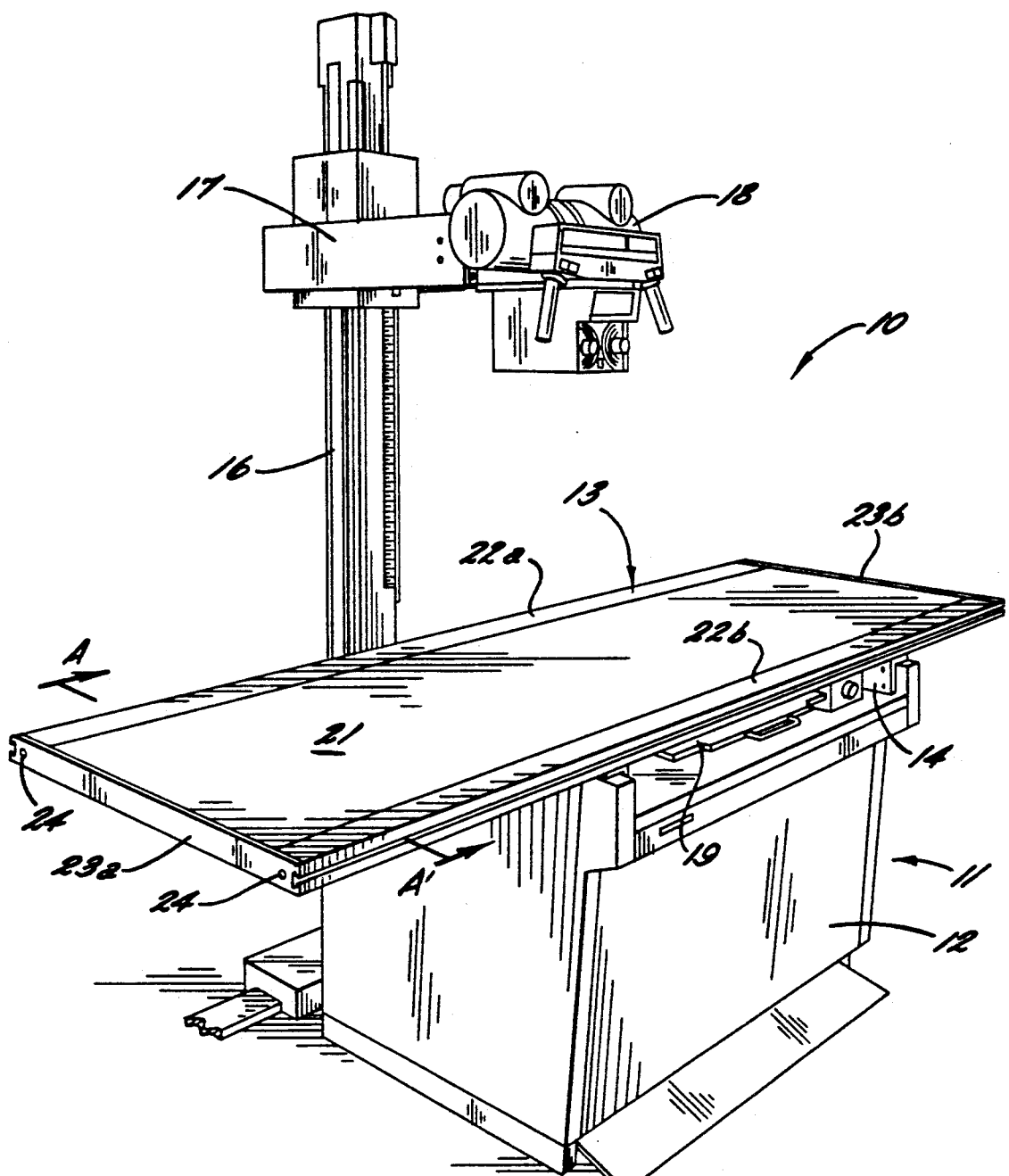
FIG. 1 is a perspective view of an x-ray apparatus having a flat top table according to the present invention.

Referring now to FIG. 1, a radiographic system, and in particular an x-ray system having a flat top radiographic table according to the present invention is shown. X-ray system 10 includes an x-ray table 11 having a base 12 and a table top 13. The base 12 may include a container or housing for a high voltage x-ray transformer and other control equipment used in the operation of the system 10. The base may also include a carriage 14 to support the table top 13 and allow for transverse movement. Other support means (not shown in FIG. 1) allow longitudinal movement of the table top 13 relative to the base 12. The system 10 may also include an x-ray tube stand 16 and a cantilevered tube arm 17 for supporting an x-ray tube or other radiographic source 18. Located below the table top 13, is an x-ray or other radiographic film carrier or cassette 19, which may include a bucky grid and related mechanisms. The detailed design of the x-ray system 10 are well known to those having skill in the art and need not be described further herein.

Still referring to FIG. 1, the x-ray system 10 includes a flat radiographic table top 13. As shown, table top 13 includes a panel 21 which is preferably formed of a paper base resinous material, and is typically less than 3/16" in thickness, and is supported longitudinally by a pair of frame members 22a and 22b. The longitudinal frame members 22 grip a longitudinal side of panel 21 so that panel 21 need not be supported at the center. A pair of end frame members 23a, 23b maintain the longitudinal frame members 22a, 22b separated from one another so that the longitudinal frame members can support the panel therebetween. Typically, the end frame members 23 are configured so that during assembly they place the panel 21 in tension. However, it will be understood by those having skill in the art that the frame members 22, 23 need not be assembled to produce tension on panel 21. Rather, the gripping force of the frame members may only produce the tension on the panel 21 when a patient is placed on the panel. Mounting screws 24 or other means attach the end frame members 23 to the longitudinal frame members 22.

According to the invention, and as illustrated in FIG. 1, the panel 21 is free of support from the longitudinal frame members 22 at the top surface thereof, so that the top surface of panel 21 and the top surfaces of longitudinal frame members 22 are coplanar, and provide a flat-top radiographic table. Patient transfer to and from the table top 13 is eased, because the frame members 22 do not form a lip over the top of panel 21. Similarly, positioning of x-ray source 18 and x-ray film 19 is not restricted by the lip.

Referring now to FIG. 2, the detailed construction of the panel 21 according to the present invention will now be described. As shown in FIG. 2, panel 21, which is typically a paper base resinous material 3/16" or less in thickness, includes a pair of recesses therein at each longitudinal end thereof. As shown, a first recess in the form of a bevel 26 is formed in the side edge 21b and a second recess 28 is formed on the bottom surface 21c. A recess is not formed on the top surface 21a. The bevel in the side edge 21b forms an acute angle 27 between the side edge 21b and the bottom surface 21c. The second recess 28 may be a longitudinal groove formed in the bottom surface 21c.

The first and second recesses 26 and 28 may be formed during molding of panel 21. Preferably, however, they may be machined into the panel after the panel has been formed using well known cutting techniques. As will be described below, the first and second recesses 26 and 28 mate with first and second projections in the longitudinal frame members 22 so that the panel may be gripped without requiring the top thereof to be gripped.

Referring now to FIG. 3, a first embodiment of a longitudinal frame member 22 according to the present invention will be described. As illustrated in FIG. 3, longitudinal frame member 22 includes a top surface 31 and a bottom surface 32. The longitudinal frame member 22 is adapted for containing a pair of rollers 33 or other means for movably supporting the frame member 22 along the carriage 14 for movement therealong, according to well known designs. The frame member also includes an accessory holder 34 allowing accessory attachment.

The top surface 31 also includes a recessed ledge 36 which includes a ledge side surface 37 and a ledge top surface 38. The ledge side surface 37 is oriented or beveled relative to the ledge top surface 38 at the same acute angle 27 as the bevel 21b in the panel 21 (FIG. 2). Also included on the top surface 38 of the ledge is a projection 39 which is oriented relative to the ledge side surface and is shaped and sized to conform to the recess 28 in the panel 21 (FIG. 2). As illustrated in FIG. 3, the projection 39 is a rectangular projection but other shaped projections may also be used. The thickness Y of ledge 36 is designed to be equal to the thickness Y of panel 21. Accordingly, when the panel 21 of FIG. 2 is mounted on the longitudinal frame member 22 of FIG. 3, the top 21a of panel 21 and the top 31 of frame member 22 lie in a single plane to provide a flat top radiographic table.

Referring now to FIG. 4, the assembly of panel 21 and frame members 22 (FIGS. 2 and 3 respectively) will be described. As shown in FIG. 4, the panel 21 may be longitudinally slid along the ledge 36 of frame member 22 with the bevel 21b of the panel mating to the side 37 of ledge 38 and the projection 39 mating to the recess 28 in the panel 21. See FIG. 5. As illustrated in FIG. 4, projection 39 is typically a longitudinal tongue and recess 28 is a matching longitudinal groove. However, a series of discrete projections and recesses may also be provided. If discrete projections and recesses are provided, the panel 21 may be snapped into longitudinal frame member 22.

Continuing with the description of FIG. 4, after the panel 21 is slid into longitudinal frame member 22 end frame member 23 is attached thereto using screw 24. As known to one having skill in the art, the size of end frame member 23 and panel 21, and the location of screws 24 may be designed so that when screws 24 are tightened, the grip of frame members 23 maintain panel 21 in tension. As shown, the end frame member top surface 23a is typically also coplanar with the top surface of the panel 21.

Referring once again to FIG. 5, it will be understood by those having skill in the art that frame member 22 may be a two piece frame member having separate mating piece 25 which may include one or more mating surfaces 29. This two piece frame member is functionally equivalent to a one piece frame member. If a two piece frame member is used, the mating piece 25 may be slid onto panel 21 and then the assembled panel and mating piece may be slid into member 22.

Figure 6:
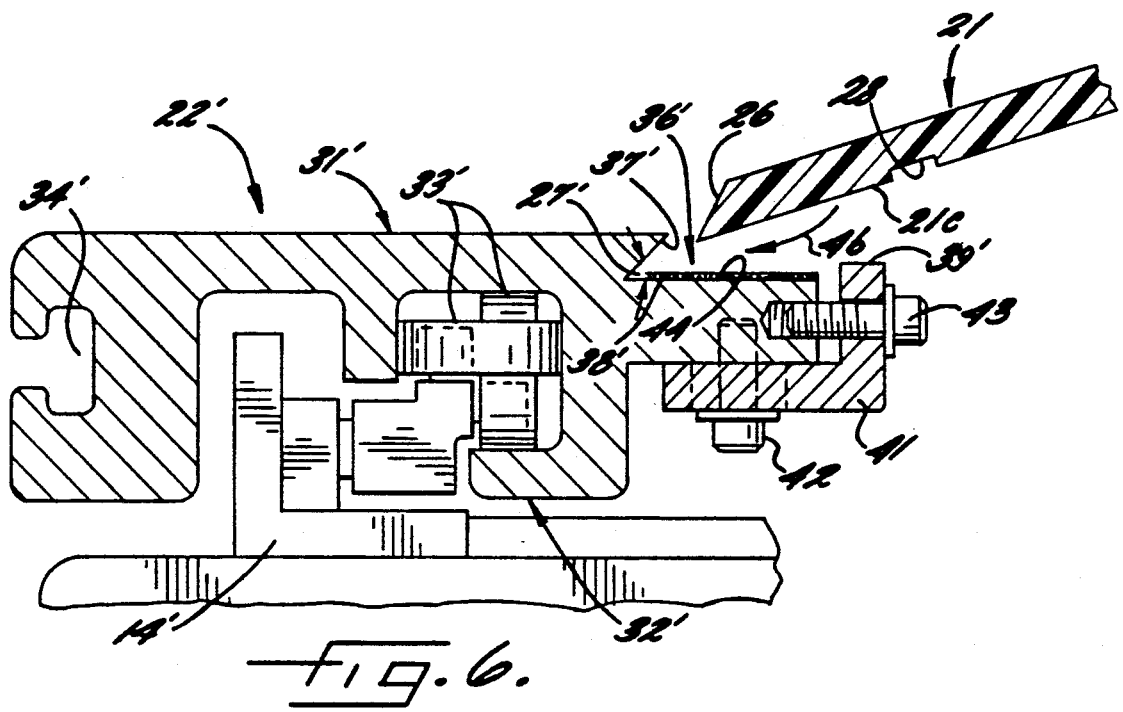
FIG. 6 is a cross-sectional view of a second embodiment of a longitudinal frame member of FIG. 1 and the thin table top of FIG. 2.

Referring now to FIG. 6, a second embodiment of the longitudinal frame member 22 is shown. This longitudinal frame member 22 includes a moveable second projection, so that the panel may be assembled to frame member without longitudinal sliding and then the projection may be moved to grip the panel. Since longitudinal sliding is not required, an adhesive, such as double sided adhesive tape, may be placed between the panel and longitudinal frame member for added mechanical strength. The tape can prevent the panel member from inadvertently being popped out from underneath the table. In FIG. 6, like elements to those in FIG. 3 will be indicated by a prime(') and will not be described again.

As shown in FIG. 6, top surface 38' of ledge 36' includes a moveable projection 39'. The moveable projection may be provided by an "L" shaped longitudinally extending member 41 which may be attached to frame member 22' using vertical screws 42 and horizontal screws 43. It will be understood by those having skill in the art that other fastening means may be provided and that other forms of moveable projections 39' may be provided. As also shown in FIG. 6, double sided adhesive tape 44 or other suitable adhesive may be provided on the top surface 38' of member 36'. Adhesive (not shown) may also be provided on the bottom surface 21C of panel 21.

In assembly, the panel 21 is inserted into ledge 36' of frame member 22' along the direction shown by arrow 46. In contrast with FIG. 4, the panel need not be longitudinally slid into the frame member. Accordingly, adhesive may be used to provide added mechanical security between panel 21 and frame member 22'.

Figure 7:
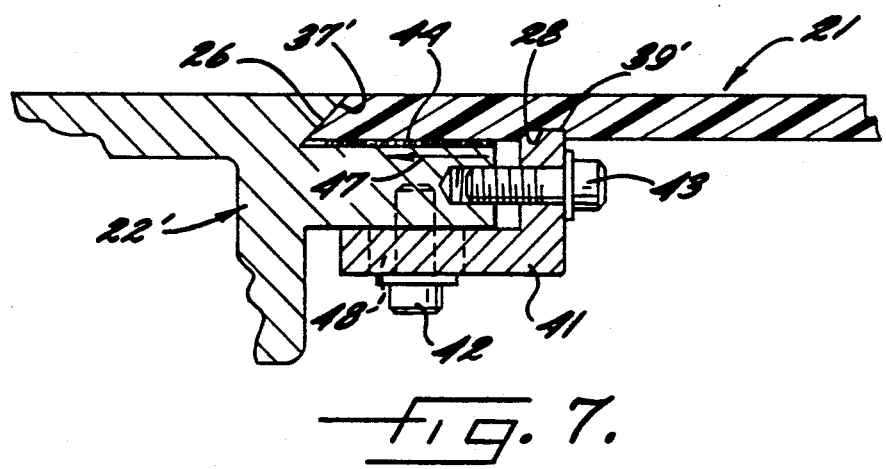
FIG. 7 is a cross sectional view of the table top panel of FIG. 2 and the frame member of FIG. 6, assembled together.

Referring to FIG. 7, after panel 21 is mounted on frame member 22' in the appropriate position, screws 42 and 43 may be tightened to mate projection 39' to recess 28. It will be understood by those having skill in the art that screws 42 and 43 are preferably located so that tightening of screw 43 forces panel 21 in the direction of arrow 47, towards ledge side 37' to force the side edge of panel 21 into the ledge side. In particular, an elongated bore 48 may be provided for screw 42 to allow sliding of member 41 in the direction of arrow 47. The embodiment of FIGS. 6–7 may provide more gripping force than the embodiment of FIGS. 3–5, at the expense of more parts and slightly more complex assembly.

Accordingly, a flat top radiographic table is provided because the panel top need not be gripped by the longitudinal frame members. The flat top radiographic table simplifies transfer of the patient to or from the table, and positioning of the x-ray source and x-ray film during radiographic or other medical procedures.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed:

1. A table top for supporting a patient during a radiographic examination, comprising:
    a panel, having parallel top and bottom surfaces, opposite ends and opposite side edges;
    a pair of frame members extending along respective ones of said side edges of said panel, said frame members being thick compared to said panel, each of said frame members including means for gripping an adjacent side edge and bottom surface of said panel, said gripping means being free of said top surface of said panel.

2. The table top of claim 1 further comprising means, extending along each of said ends of said panel, for interconnecting said frame members so as to support said panel therebetween.

3. The table top of claim 1 wherein said panel includes a first recess on each of said side edges and a second recess on said panel bottom surface adjacent each panel side edge, and wherein said gripping means comprises a pair of projections for gripping said panel at said first and second recesses.

4. The table top of claim 3 wherein said first recess comprises an elongated bevel in each panel side edge, and said second recess comprises an elongated groove in said panel bottom adjacent each panel side edge.

5. The table top of claim 3 wherein at least one of said pair of projections is moveable relative to said frame member.

6. The table top of claim 1 in combination with a base and means for moveably supporting said table top on said base, to provide a patient supporting table.

7. The table top of claim 1 in combination with a radiographic source and a radiographic image recorder holding means, said radiographic source and said radiographic image recorder holding means being oriented relative to said table top such that said radiographic source emits radiation which passes through at least part of a patient on said table top and impinges onto said radiographic image recorder holding means.

8. A table top for supporting a patient during a radiographic examination, comprising:
   a panel, having parallel top and bottom surfaces, opposite ends and opposite side edges;
   a pair of frame members extending along respective ones of said side edges of said panel, said frame members each having a top and a bottom surface, said frame members being thick compared to said panel, said panel and said frame members each including cooperating mating surfaces thereon for mating to one another such that said frame member top surfaces and said panel top surface are coplanar, to provide a flat radiographic table top.

9. The table top of claim 8 further comprising means, extending along each of said ends of said panel, for interconnecting said frame members so as to support said panel therebetween.

10. The table top of claim 8 wherein said frame member mating surfaces each comprise a pair of projections, and wherein said panel mating surfaces each comprise a pair of recesses, said pair of projections mating with said pair of recesses.

11. The table top of claim 10 wherein said pair of recesses comprises a first recess on each of said panel side edges and a second recess on said panel bottom surface adjacent each panel side edge, and wherein said pair of projections comprise a pair of projections in said frame member, between the top and bottom thereof.

12. The table top of claim 11 wherein said first recess comprises an elongated bevel in each of said panel side edges, and said second recess comprises an elongated groove in said panel bottom surface adjacent each panel edge side.

13. The table top of claim 11 wherein at least one of said pair of projections is moveable relative to said frame member.

14. The table top of claim 8 in combination with a base and means for moveably supporting said table top on said base, to provide a patient supporting table.

15. The table top of claim 8 in combination with a radiographic source and a radiographic image recorder holding means, said radiographic source and said radiographic image recorder holding means being oriented relative to said table top such that said radiographic source emits radiation which passes through at least part of a patient on said table top and impinges onto said radiographic image recorder holding means.

16. A table top for supporting a patient during a radiographic examination, comprising:
   a panel, having parallel top and bottom surfaces, opposite ends and opposite side edges, said side edges being beveled to define an acute angle with said bottom surface, said bottom surface including a pair of recesses therein, each of said recesses being located a predetermined distance from an adjacent side edge;
   a pair of frame members, extending longitudinally along respective ones of said side edges of said panel, each of said frame members having a top and a bottom surface, and a ledge in the top surface thereof, said ledge including a side ledge surface and a top ledge surface, said side ledge surface being undercut at said acute angle relative to said top ledge surface and receiving the adjacent panel side edge therein, said top ledge surface including a projection located said predetermined distance from said side ledge surface and projecting into the recess of the adjacent panel side edge, the thickness of said panel being equal to the depth of said ledge such that said top surface of said panel and said top surfaces of said frame members are coplanar to provide a flat radiographic table top.

17. The table top of claim 16 further comprising means, extending along each of said ends of said panel, for interconnecting said frame members so as to support said panel therebetween.

18. The table top of claim 16 wherein said pair of recesses comprises a pair of longitudinal grooves and wherein said projection comprises a longitudinal tongue.

19. The table top of claim 16 wherein said projection is moveable toward and away from said side ledge surface.

20. The table top of claim 19 further comprising tightening means, mechanically coupled between said movable projection and said frame member, for moving said movable projection toward said side ledge surface to thereby force said panel side edge into said side ledge surface.

21. The table top of claim 19 wherein said moveable projections each comprise a movable L-shaped member, with one leg of said L-shaped member extending parallel to said ledge top surface and the other leg of said L-shaped member extending perpendicular to said ledge top surface, said other leg of said L-shaped member forming said moveable projection.

22. The table top of claim 16 in combination with a base and means for moveably supporting said table top on said base, to provide a patient supporting table.

23. The table top of claim 16 in combination with a radiographic source and a radiographic image recorder holding means, said radiographic source and said radiographic image recorder holding means being oriented relative to said table top such that said radiographic source emits radiation which passes through at least part of a patient on said table top and impinges onto said radiographic image recorder holding means.

* * * * *